(12) United States Patent
Huebner et al.

(10) Patent No.: US 6,610,869 B1
(45) Date of Patent: Aug. 26, 2003

(54) BRANCHED, SUBSTANTIALLY UNSATURATED ESTER OILS

(75) Inventors: Norbert Huebner, Duesseldorf (DE); Alfred Westfechtel, Hilden (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 0 days.

(21) Appl. No.: 10/049,921
(22) PCT Filed: Aug. 11, 2000
(86) PCT No.: PCT/EP00/07848
§ 371 (c)(1), (2), (4) Date: Jun. 4, 2002
(87) PCT Pub. No.: WO01/14309
PCT Pub. Date: Mar. 1, 2001

(30) Foreign Application Priority Data

Aug. 20, 1999 (DE) .......................... 199 39 566

(51) Int. Cl.⁷ .............................. C07C 51/36
(52) U.S. Cl. ..................... 554/142; 554/141
(58) Field of Search .................. 554/141, 142

(56) References Cited

U.S. PATENT DOCUMENTS

| | | |
|---|---|---|
| 4,172,887 A | 10/1979 | Vanlerberghe et al. |
| 5,399,792 A | 3/1995 | Demmering |
| 5,672,781 A | 9/1997 | Koehler et al. |
| 5,705,169 A | 1/1998 | Stein et al. |
| 5,730,960 A | 3/1998 | Stein et al. |
| 6,037,487 A | 3/2000 | Habeck et al. |
| 6,193,960 B1 | 2/2001 | Metzger et al. |
| 6,229,056 B1 | 5/2001 | Ansmann et al. |

FOREIGN PATENT DOCUMENTS

| | | | |
|---|---|---|---|
| DE | 11 65 574 | | 8/1960 |
| DE | 20 24 051 | | 5/1970 |
| DE | 43 35 781 | | 10/1993 |
| DE | 44 22 858 | | 6/1994 |
| DE | 44335781 | * | 4/1995 |
| DE | 4422858 | * | 7/1995 |
| DE | 19712033 | | 3/1997 |
| EP | 0 602 108 | | 8/1992 |
| EP | 0 693 471 | | 7/1995 |
| EP | 0 694 521 | | 7/1995 |
| EP | 0 818 450 | | 7/1997 |
| FR | 2 252 840 | | 11/1974 |
| GB | 962 919 | | 8/1961 |
| GB | 1 333 475 | | 5/1971 |

OTHER PUBLICATIONS

A. Behr et al., *Katalytische Oligomerisierung von Fettstoffen*, Fat Sci. Technol. 93, pp 340–345 (1991).
Moehring et al., *Produkte der Dimerisierung ungesaettigter Fettsaeuren VII: Kinetische Untersuchung der Mono– und Dimeren, die bei der Dimerisierung von Oelsaeure entstehen*, Fat Sci. Technol. 94, pp 41–46 (1992).
Moehring et al., *Produkte der Dimerisierung ungesaettigter Fettsaeuren VIII: Ueber die Zusammensetzung der Fraktion der "Intermediates" bei der Fettsaeuredimerisierung*, Fat Sci. Technol. 94, pp 241–245, (1992).
Todd et al., "Volatile silicon fluids for cosmetic formulations", pp. 29–32, vol. 91, Cosmetics & Toiletries, (1976).
Lochhead et al., *Encyclopedia of Polymers and Thickeners for Cosmetics*, Cosm.Toil. 108, pp 95–114, 116–124, 127–130, 132–135 (1995).
P. Finkel, *Formulierung kosmetischer Sonnenschutzmittel*, SÖFW–Journal 122, pp 543–546, 548 (1996).
Dritte, *Kosmetische Farbemittel*, Farbstoffkomission der Deutschen Forschungsgemeinschaft, Verlag Chemie, Weinheim, pp. 81–106, (1984).

\* cited by examiner

*Primary Examiner*—Deborah D. Carr
(74) *Attorney, Agent, or Firm*—John E. Drach; Steven J. Trzaska

(57) ABSTRACT

A process for making branched, substantially unsaturated ester oils involving: (a) providing an unsaturated $C_{16-22}$ fatty acid; (b) dimerizing the unsaturated $C_{16-22}$ fatty acid; (c) removing a monomer fraction accumulating during dimerization, the monomer fraction containing branched, substantially unsaturated fatty acids; (d) converting the branched, substantially unsaturated fatty acids contained in the monomer fraction into corresponding branched, substantially unsaturated fatty acid methyl esters having double bonds; (e) hydrogenating the branched, substantially unsaturated fatty acid methyl esters, with their double bonds intact, to form corresponding branched, substantially unsaturated fatty alcohols; and (f) esterifying the branched, substantially unsaturated fatty alcohols to form the branched, substantially unsaturated ester oils.

18 Claims, No Drawings

BRANCHED, SUBSTANTIALLY UNSATURATED ESTER OILS

BACKGROUND OF THE INVENTION

This invention relates generally to cosmetic oil components and, more particularly, to substantially unsaturated ester oils which, through the presence of branches in the hydrocarbon chain, are distinguished from linear homologs by significantly improved properties, to a process for their production and to their use for the production of surface-active compositions.

PRIOR ART

Ester oils are understood by the expert to be cosmetic oil components where the acid and alcohol component together contain at least 20 carbon atoms and which are liquid at room temperature. The favorable properties of these substances are linked to the presence of one or more double bonds in the acid and/or alcohol component which also presents problems because the ester oils readily fall victim to autoxidation, discolor and undergo unwanted chemical changes (for example formation of peroxides and hydroperoxides).

Accordingly, it is clear that there is a need on the market for ester oils or suitable substitutes which possess at least equivalent performance properties. However, more or less pure isostearyl alcohol esters have hitherto been the only alternatives to unsaturated ester oils. To produce these more or less pure isostearyl alcohol esters, however, oleic acid first has to be dimerized, the fraction of monomeric branched fatty acids separated off, hydrogenated and subjected to fractional crystallization, the liquid fraction accumulating, which is rich in isostearic acid, has to be removed and esterified with methanol and the esters obtained subsequently hydrogenated to form the alcohols which, finally, are again converted into esters by condensation with suitable acids.

The process described above is technically complicated by the two hydrogenation steps and, in the isostearyl alcohol sulfates, provides substitutes which can only replace the unsaturated fatty alcohols to a limited extent. Accordingly, the problem addressed by the present invention was to provide unsaturated ester oils which would be distinguished by improved performance properties and preferably by higher oxidation stability.

DESCRIPTION OF THE INVENTION

The present invention relates to branched, substantially unsaturated ester oils which are obtainable by
(a) dimerizing unsaturated $C_{16-22}$ fatty acids in known manner,
(b) removing the monomer fraction accumulating in the dimerization step,
(c) converting the branched, substantially unsaturated fatty acids present in this fraction into the corresponding fatty acid methyl esters,
(d) hydrogenating the branched, substantially unsaturated fatty acid methyl esters with the double bonds intact to form the corresponding branched, substantially unsaturated fatty alcohols and
(e) esterifying the branched, substantially unsaturated fatty alcohols in known manner.

It has surprisingly been found that the branched, substantially unsaturated ester oils have distinctly improved autoxidation stability compared with linear homologs having the same chain length and the same iodine value. Further advantages include improved spreading behavior and easier biodegradability.

The present invention also relates to a process for the production of branched, substantially unsaturated ester oils in which
(a) unsaturated $C_{16-22}$ fatty acids are dimerized in known manner,
(b) the monomer fraction accumulating in the dimerization step is removed,
(c) the branched, substantially unsaturated fatty acids present in this fraction are converted into the corresponding fatty acid methyl esters,
(d) the branched, substantially unsaturated fatty acid methyl esters are hydrogenated with the double bonds intact to form the corresponding branched, substantially unsaturated fatty alcohols which are then
(e) esterified in known manner.

Production of the Fatty Alcohols

The dimerization of fatty acids and the recovery of monomer fatty acids from the dimers is sufficiently well-known from the prior art, cf. for example the overviews by A. Behr et al. [*Fat Sci. Technol.* 93, 340 (1991)] and by H. Möhring et al. [ibid. 94, 41 (1992) and 94, 241 (1992)]. The sequence of steps (a) to (d) gives branched, substantially unsaturated fatty alcohols with iodine values of 45 to 85 on the basis of dimerized, preferably monounsaturated $C_{16-22}$ fatty acids, i.e. oleic acid, elaidic acid, petroselic acid, gadoleic acid and erucic acid and mixtures thereof. This is without doubt entirely adequate for a number of applications. However, in cases where fatty compounds with a relatively high content of unsaturated compounds are required, it is advisable to subject the monomer fraction accumulating in the dimerization step to fractional crystallization and then to subject the liquid phase obtained to esterification, optionally after distillation. The fatty acid obtained and its methyl esters represent an already fairly pure isooleic acid or isooleic acid methyl ester with iodine values of 75 to 95. In any event, it is advisable to subject the methyl esters and/or the fatty alcohols to distillation and/or fractional crystallization ("winterizing"). The esterification of the fatty acids with methanol is carried out by known methods and is intended to produce methyl esters which are comparatively easy to hydrogenate. Instead of the methyl esters, other lower alkyl esters, for example ethyl, propyl or butyl esters, may of course also be produced and subsequently hydrogenated. The choice of the alcohol is basically not critical and is solely determined by economic criteria and availability. Instead of the methyl or lower alkyl esters, it is also possible in principle directly to esterify the fatty acids, although this does involve the use of special catalysts which do not form salts with the acids. In addition, the reactor material has to be corrosion-resistant. The hydrogenation of the unsaturated methyl esters to form the corresponding alcohols may also be carried out in known manner. Corresponding processes and catalysts, particularly those based on copper and zinc, are disclosed for example in the following documents: DE 43 357 81 C1, EP 0 602 108 B1, U.S. Pat. Nos. 3,193,586 and 3,729,520 (Henkel); reference is expressly made to the disclosures of these documents.

Esterification

The esterification may be carried out, for example, with monocarboxylic acids corresponding to formula (I):

$$R^1CO\text{—}OH \qquad (I)$$

in which $R^1CO$ is a linear or branched, aliphatic or aromatic, saturated or unsaturated acyl group containing 1 to 22 carbon atoms. Typical examples are lower aliphatic carboxylic acids containing 1 to 5 carbon atoms, such as formic acid, acetic acid, propionic acid, butyric acid and valeric acid. Also suitable are fatty acids containing 6 to 22 carbon atoms such as, for example, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms such as, for example, coconut fatty acid, palm oil fatty acid, palm kernel oil fatty acid or tallow fatty acid are preferred. Examples of aromatic carboxylic acids are benzoic acid and cinnamic acid. Besides the monobasic carboxylic acids, polybasic, optionally hydroxy substituted carboxylic acids containing 2 to 12 carbon atoms, for example succinic acid, maleic acid, adipic acid, phthalic acid, malic acid, tartaric acid and citric acid and mixtures thereof, are also suitable. The esterification may be carried out in known manner, i.e. in the presence of alkaline or acidic catalysts, one component in excess and continuous removal of the water of reaction from the equilibrium.

Commercial Applications

The new branched substantially unsaturated ester oils are distinguished by particular stability to oxidation and are therefore suitable as oil components for the production of cosmetic and/or pharmaceutical preparations in which they may be present in quantities of 1 to 90% by weight, preferably 5 to 50% by weight and more particularly 10 to 35% by weight.

Cosmetic and/or Pharmaceutical Preparations

The branched, substantially unsaturated ester oils according to the invention may be used for the production of cosmetic and/or pharmaceutical preparations, for example hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil componentss, emulsifiers, superfatting agents, pearlizing waxes, consistency factors, thickeners, polymers, silicone compounds, fats, waxes, stabilizers, biogenic agents, deodorants, antiperspirants, anti-dandruff agents, film formers, swelling agents, UV protection factors, antioxidants, hydrotropes, preservatives, insect repellents, self-tanning agents, solubilizers, perfume oils, dyes and the like as further auxiliaries and additives.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C^{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/tri-glyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C^{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Suitable emulsifiers are, for example, nonionic surfactants from at least one of the following groups:

- products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;
- alkyl and/or alkenyl oligoglycosides containing 8 to 22 carbon atoms in the alkyl group and ethoxylated analogs thereof;
- products of the addition of 1 to 15 moles of ethylene oxide with castor oil and/or hydrogenated castor oil;
- products of the addition of 15 to 60 moles of ethylene oxide with castor oil and/or hydrogenated castor oil;
- partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof with 1 to 30 moles of ethylene oxide;
- partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof with 1 to 30 moles of ethylene oxide;

mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, polyalkylene glycols and glycerol carbonate.

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C^{12/18}$ fatty acid monoesters and diesters of addition products of ethylene oxide with glycerol are known as refatting agents for cosmetic formulations from DE 20 24 051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glucoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide with the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 moles of ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Finally, other suitable emulsifiers are cationic surfactants, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in *Cosm. Toil.* 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acidand salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, nettle oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, limeblossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency promoters,
auxiliaries in the form of, for example, thickeners or complexing agents and/or
nonaqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox and zinc pyrithione.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable swelling agents for aqueous phases are montmorillonites, clay minerals, Pemulen and alkyl-modified Carbopol types (Goodrich). Other suitable polymers and swelling agents can be found in R. Lochhead's review in *Cosm. Toil.* 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, fur-furylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetyl-aminopropionate. A suitable self-tanning agent is dihydroxyacetone.

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "*Kosmetische Färbemittel*" of the *Farbstoffkommission der Deutschen Forschungs-gemeinschaft*, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

Example 1

23 kg of the monomer fatty acid Edenor® 935 (Henkel KGaA) were esterified with 20 kg of methanol for 2 h at 240° C./100 bar. After removal of the water/methanol mixture, the same quantity of fresh methanol was added and the procedure was repeated twice. The ester thus obtained had an acid value of 0.8. The methyl ester was hydrogenated on a fixed-bed Zn/Cr catalyst with the double bond intact. The throughput of methyl ester was 0.5 unit by volume per hour, based on the total volume of the reactor. After removal of the methanol, the crude alcohol was distilled (3% first runnings, 90% main runnings, 6% residue). The resulting alcohol had a hydroxyl value of 192, a saponification value of 0.9 and an iodine value of 74 (solidus point 25.8° C.). 283.3 g of technical oleic acid (Edenor® PK 1805, Henkel KGaA) were esterified under nitrogen with 292 g of the isooleyl alcohol previously obtained and 0.17 g of tin(II) oxalate in a stirred reactor with a water separator at temperatures of 200 to 220° C. An acid value of 10 was reached after 2 h. Esterification was then continued for another hour at 220° C. in a water jet vacuum. The resulting isooleyl oleate had an acid value of 2.5.

Example 2

Monomer fatty acid was substantially freed from straight-chain saturated fatty acids by crystallization from methanol/water (Emersol process). Around 20% by weight of fatty acid, predominantly palmitic and stearic acid, was removed in this way. The liquid fatty acid mixture obtained after removal of the solvent by distillation had a titer of 5° C. and was first converted into the methyl ester and then hydrogenated to the unsaturated fatty alcohol in the same way as in Example 1. The unsaturated fatty alcohol had a hydroxyl value of 191, a saponification value of 1.7 and an iodine value of 87 (solidus point 3.8° C.). 283.3 g of technical elaidic acid were esterified under nitrogen with 292 g of the isooleyl alcohol previously obtained and 0.17 g of tin(II) oxalate in a stirred reactor with a water separator at temperatures of 200 to 220° C. An acid value of 10 was reached after 2 h. Esterification was then continued for another hour at 220° C. in a water jet vacuum. The resulting isooleyl elaidate had an acid value of 2.5.

Table 1 below shows a number of formulation examples.

TABLE 1

| Cosmetic preparations (water, preservative to 100% by weight) | | | | | | | | | | |
|---|---|---|---|---|---|---|---|---|---|---|
| Composition (INCI) | 1 | 2 | 3 | 4 | 5 | 6 | 7 | 8 | 9 | 10 |
| Texapon ® NSO Sodium Laureth Sulfate | 15.0 | 15.0 | 10.0 | — | 20.0 | 8.0 | — | — | — | — |
| Texpon ® K 14 S Sodium Myreth Sulfate | — | — | — | — | — | — | — | — | 8.0 | 15.0 |

TABLE 1-continued

Cosmetic preparations (water, preservative to 100% by weight)

| | | | | | | | | | | |
|---|---|---|---|---|---|---|---|---|---|---|
| Fatty alcohol sulfate of Example 1 | 5.0 | 5.0 | 2.4 | 1.0 | 5.0 | 3.0 | 1.0 | 1.0 | 3.0 | 8.0 |
| Texapon ® SB 3<br>Disodium Laureth Sulfosuccinate | — | — | — | — | — | 7.0 | — | — | — | — |
| Plantacare ® 818<br>Coco Glucosides | 5.0 | 5.0 | 4.0 | — | — | — | — | — | 6.0 | 4.0 |
| Plantacare ® 2000<br>Decyl Glucoside | — | — | — | — | 5.0 | 4.0 | — | — | — | — |
| Plantacare ® PS 10<br>Sodium Laureth Sulfate (and) Coco Glucosides | — | — | — | 40.0 | — | — | 16.0 | 17.0 | — | — |
| Dehyton ® PK 45<br>Cocamidopropyl Betaine | 20.0 | 20.0 | — | — | 8.0 | — | — | — | — | 7.0 |
| Eumulgin ® B1<br>Ceteareth-12 | — | — | — | — | 1.0 | — | — | — | — | — |
| Eumulgin ® B2<br>Ceteareth-20 | — | — | — | 1.0 | — | — | — | — | — | — |
| Lameform ® TGI<br>Polyglyceryl-3 Isostearate | — | — | — | 4.0 | — | — | — | — | — | — |
| Dehymuls ® PGPH<br>Polyglyceryl-2 Dipolyhydroxystearate | — | — | 1.0 | — | — | — | — | — | — | — |
| Monomuls ® 90-L 12<br>Glyceryl Laurate | — | — | — | — | — | — | — | — | 1.0 | 1.0 |
| Cetiol ® HE<br>PEG-7 Glyceryl Cocoate | — | 0.2 | — | — | — | — | — | — | — | — |
| Eutanol ® G<br>Octyldodecanol | — | — | — | 1.0 | — | — | — | — | — | — |
| Ester of Example H1 | 1.0 | 1.0 | 1.0 | 1.0 | 1.0 | 1.0 | 1.0 | 1.0 | 1.0 | 1.0 |
| Nutrilan ® Keratin W<br>Hydrolyzed Keratin | — | — | — | — | — | — | — | — | 2.0 | 2.0 |
| Nutrilan ® I<br>Hydrolyzed Collagen | 1.0 | — | — | — | — | 2.0 | — | 2.0 | — | — |
| Lamesoft ® LMG<br>Glyceryl Laurate (and) Potassium Cocoyl Hydrolyzed Collagen | — | — | — | — | — | — | — | — | 1.0 | 5.0 |
| Gluadin ® WK<br>Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM<br>Glycol Distearate (and) Laureth-4 (and) Cocamidopropyl Betaine | 5.0 | 3.0 | 4.0 | — | — | — | — | 3.0 | 3.0 | — |
| Panthenol | — | — | 1.0 | — | — | — | — | — | — | — |
| Arlypon ® F<br>Laureth-2 | 2.6 | 1.6 | — | 1.0 | 1.5 | — | — | — | — | — |
| Highcareen ® GS<br>Betaglucan | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerin (86% by weight) | — | 5.0 | — | — | — | — | — | 1.0 | 3.0 | — |

| Composition (INCI) | 11 | 12 | 13 | 14 | 15 | 16 | 17 | 18 | 19 | 20 |
|---|---|---|---|---|---|---|---|---|---|---|
| Texapon ® NSO<br>Sodium Laureth Sulfate | — | 22.0 | 22.0 | — | 20.0 | — | — | — | — | — |
| Plantacare ® 818<br>Coco Glucosides | — | 10.0 | — | — | 20.0 | — | — | — | — | — |
| Plantacare ® PS 10<br>Sodium Laureth Sulfate (and) Coco Glucosides | 22.0 | — | 5.0 | 22.0 | — | — | — | — | — | — |
| Dehyton ® PK45<br>Cocamidopropyl Betaine | 15.0 | 10.0 | 15.0 | 15.0 | 20.0 | — | — | — | — | — |
| Emulgade ® SE<br>Glyceryl Stearate (and) Cetearth 12/20 (and) Cetearyl Alcohol (and) Cetyl Palmitate | — | — | — | — | — | 5.0 | 5.0 | 4.0 | — | — |
| Lameform ® TGI<br>Polyglyceryl-3 Isostearate | — | — | — | — | — | — | — | — | 4.0 | — |
| Dehymuls ® PGPH<br>Polyglyceryl-2 Dipolyhydroxystearate | — | — | — | — | — | — | — | — | — | 4.0 |
| Monomuls ® 90-O 18<br>Glyceryl Oleate | — | — | — | — | — | — | — | — | 2.0 | — |
| Cetiol ® HE<br>PEG-7 Glyceryl Cocoate | 2.0 | — | — | 2.0 | 5.0 | — | — | — | — | 2.0 |
| Cetiol ® OE<br>Dicaprylyl Ether | — | — | — | — | — | — | — | — | 5.0 | 6.0 |
| Cetiol ® PGL<br>Hexyldecanol (and) Hexyldecyl Laurate | — | — | — | — | — | — | — | 3.0 | 10.0 | 9.0 |
| Cetiol ® SN<br>Cetearyl Isononanoate | — | — | — | — | — | 3.0 | 3.0 | — | — | — |
| Cetiol ® V<br>Decyl Oleate | — | — | — | — | — | 3.0 | 3.0 | — | — | — |

TABLE 1-continued

| Cosmetic preparations (water, preservative to 100% by weight) | | | | | | | | | | |
|---|---|---|---|---|---|---|---|---|---|---|
| Myritol ® 318 Coco Caprylate Caprate | — | — | — | — | — | — | — | 3.0 | 5.0 | 5.0 |
| Ester of Example H2 | 1.0 | 1.0 | 1.0 | 1.0 | 1.0 | 1.0 | 1.0 | 1.0 | 1.0 | 1.0 |
| Bees Wax | — | — | — | — | — | — | — | — | 7.0 | 5.0 |
| Nutrilan ® Elastin E20 Hydrolyzed Elastin | — | — | — | — | — | 2.0 | — | — | — | — |
| Nutrilan ® I-50 Hydrolyzed Collagen | — | — | — | — | 2.0 | — | 2.0 | — | — | — |
| Gluadin ® AGP Hydrolyzed Wheat Gluten | 0.5 | 0.5 | 0.5 | — | — | — | — | 0.5 | — | — |
| Gluadin ® WK Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM Glycol Distearate (and) Laureth-4 (and) Cocamidopropyl Betaine | 5.0 | — | — | 5.0 | — | — | — | — | — | — |
| Highcareen ® GS Betaglucan | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Magnesium Sulfate Hepta Hydrate | — | — | — | — | — | — | — | — | 1.0 | 1.0 |
| Glycerin (85% by weight) | — | — | — | — | — | 3.0 | 3.0 | 5.0 | 5.0 | 3.0 |

1–4 "two-in-one" shower bath,
5–10 shampoo
11–15 foam bath,
16 soft cream,
17, 18 moisturizing emulsion,
19, 20 night cream

What is claimed is:

1. A process for making branched, substantially unsaturated ester oils comprising:
   (a) providing an unsaturated $C_{16-22}$ fatty acid;
   (b) dimerizing the unsaturated $C_{16-22}$ fatty acid;
   (c) removing a monomer fraction accumulating during dimerization, the monomer fraction containing branched, substantially unsaturated fatty acids;
   (d) converting the branched, substantially unsaturated fatty acids contained in the monomer fraction into corresponding branched, substantially unsaturated fatty acid methyl esters having double bonds;
   (e) hydrogenating the branched, substantially unsaturated fatty acid methyl esters, with their double bonds intact, to form corresponding branched, substantially unsaturated fatty alcohols; and
   (f) esterifying the branched, substantially unsaturated fatty alcohols to form the branched, substantially unsaturated ester oils.

2. The process of claim 1 wherein the monomer fraction of step (c) is fractionally crystallized prior to step (d).

3. The process of claim 1 wherein the branched, substantially unsaturated fatty acid methyl esters having double bonds of step (d) are distilled prior to step (e).

4. The process of claim 1 wherein the branched, substantially unsaturated fatty acid methyl esters having double bonds of step (d) are fractionally distilled prior to step (e).

5. The process of claim 1 wherein the branched, substantially unsaturated fatty alcohols of step (f) are esterified with an esterification component selected from the group consisting of a monocarboxylic acid, a dicarboxylic acid, a hydroxcarboxylic acid, and mixtures thereof.

6. A cosmetic composition containing the branched, substantially unsaturated ester oils of claim 1.

7. The composition of claim 6 wherein the branched, substantially unsaturated ester oils are present in the composition in an amount of from about 1 to 90% by weight, based on the weight of the composition.

8. The composition of claim 6 wherein the branched, substantially unsaturated ester oils are present in the composition in an amount of from about 5 to 50% by weight, based on the weight of the composition.

9. The composition of claim 6 wherein the branched, substantially unsaturated ester oils are present in the composition in an amount of from about 10 to 35% by weight, based on the weight of the composition.

10. A pharmaceutical composition containing the branched, substantially unsaturated ester oils of claim 1.

11. The composition of claim 10 wherein the branched, substantially unsaturated ester oils are present in the composition in an amount of from about 1 to 90% by weight, based on the weight of the composition.

12. The composition of claim 10 wherein the branched, substantially unsaturated ester oils are present in the composition in an amount of from about 5 to 50% by weight, based on the weight of the composition.

13. The composition of claim 10 wherein the branched, substantially unsaturated ester oils are present in the composition in an amount of from about 10 to 35% by weight, based on the weight of the composition.

14. The product of the process of claim 1.
15. The product of the process of claim 2.
16. The product of the process of claim 3.
17. The product of the process of claim 4.
18. The product of the process of claim 5.

* * * * *